US010409952B2

(12) United States Patent
Chen et al.

(10) Patent No.: US 10,409,952 B2
(45) Date of Patent: Sep. 10, 2019

(54) KNOWLEDGE-BASED PERSONAL INTELLIGENT HEALTH CONSULTING SYSTEM

(71) Applicant: National Taiwan University, Taipei (TW)

(72) Inventors: Chien-Chin Chen, Taipei (TW); Yea-Li Sun, Taipei (TW)

(73) Assignee: NATIONAL TAIWAN UNIVERSITY, Taipei (TW)

(*) Notice: Subject to any disclaimer, the term of this patent is extended or adjusted under 35 U.S.C. 154(b) by 988 days.

(21) Appl. No.: 14/880,714

(22) Filed: Oct. 12, 2015

(65) Prior Publication Data
US 2017/0103168 A1    Apr. 13, 2017

(51) Int. Cl.
*G16H 70/60* (2018.01)
*G06F 19/00* (2018.01)

(52) U.S. Cl.
CPC .................................. *G06F 19/324* (2013.01)

(58) Field of Classification Search
CPC ....... G06F 19/324; G16H 70/00; G16H 70/60
See application file for complete search history.

(56) References Cited

U.S. PATENT DOCUMENTS

2002/0002325 A1* 1/2002 Iliff ........................ G06Q 50/22
                                                                    600/300
2004/0242972 A1* 12/2004 Adak ...................... G06F 19/00
                                                                    600/300

* cited by examiner

*Primary Examiner* — Jonathan Durant
*Assistant Examiner* — Chad A Newton
(74) *Attorney, Agent, or Firm* — WPAT, PC

(57) ABSTRACT

The present invention provides a method for providing a knowledge-based personal intelligent health consultation, to which a medical knowledge base is constructed and utilized, and the correlations between the diseases and symptoms encompassed therein are statically and dynamically evaluated. The present invention also provides a system for providing a knowledge-based personal intelligent health consultation, in which an inference engine is configured to intelligently assess certainty values of diseases/symptoms presented in the medical knowledge base while interactively and adaptively adjust the certainty values of symptoms and possible diseases based on the instant selection of a user. Through a series of interactions, an accurate, fast, and personalized health consultation can be obtained since the user is guided to provide the right answers to the right questions proposed by the system; thus, significantly promotes the users' willingness to seek a health consultation and increases the health condition of the general public.

15 Claims, 5 Drawing Sheets

KNOWLEDGE-BASED PERSONAL INTELLIGENT HEALTH CONSULTING SYSTEM

BACKGROUND OF THE INVENTION

1. Field of the Invention

The present invention is related to a health consulting system; more specifically, the present invention is related to a knowledge-based personal intelligent health consulting system that guides a user to identify symptoms leading to possible diseases and provides relevant health information.

2. The Prior Arts

Nowadays, people often relied on Internet as the most instant, convenient, and reliable source of information when encountering health related problems. Although a vast amount of information can be obtained with ease, most health related information, whether regarding description of symptoms or diseases, is very profession-oriented. That is to say, for the general public, it is extremely mind-consuming and substantially difficult to obtain accurate and useful information due to lack of in-depth understanding of medical knowledge.

Certain healthcare advisory systems can be found on the internet, yet, for most conventional systems, information are presented in a subjective written manner. Since not all users are of medical related background and cannot provide precise description of their condition verbally, it is very unlikely for them to readily comprehend the information requested by those conventional systems and let alone fully utilize the information eventually received. Furthermore, those conventional systems usually inquire users' health related data via unilateral questionnaires. Without interactive and eliciting scenarios, this type of conventional systems cannot provide its users with intelligent, accurate, and appropriate healthcare consultation.

These setbacks of the conventional systems significantly reduce the users' willingness to seek personalized health consultation and, consequently, increase the risk of critical illnesses and the burden on healthcare resources. Thus, for the purposes of providing fast and accurate healthcare consultations and promoting awareness of personal healthcare, it is of urgent necessity for the development of an interactive, user-friendly, and knowledge-based system or method.

SUMMARY OF THE INVENTION

One aspect of the present invention is to provide a method for providing a knowledge-based personal intelligent health consultation, the method comprising: providing a symptom option list to a user terminal and receiving a symptom selection set from the user terminal; inferring at least one candidate disease from a medical knowledge base based on the symptom selection set received from the user terminal, wherein the medical knowledge base includes a vast amount of information regarding diseases and symptoms, the correlations between diseases and symptoms are specifically evaluated using a weighted AND-OR diagram; assessing a certainty value of the candidate disease; and providing a health consultation to the user terminal when the certainty value of the candidate disease exceeds a predetermined threshold value, or providing a symptom option list generated by an inference engine to the user terminal when the certainty value of the candidate disease fails to reach the predetermined threshold value.

For the method of the present invention, the inference engine interactively and adaptively adjusts the certainty values of symptoms and candidate diseases based on the symptom selection set received from the user terminal. The symptom is represented by a feature vector in the medical knowledge base, the feature vector includes at least body part, lesion, a weight of occurrence, and the certainty value of the candidate disease.

In one embodiment of the present invention, the weight of occurrence is calculated according to the uniqueness and dominance of the symptom to the disease. The symptom option list generated by the inference engine comprises at least one inferred symptom, and when more than one inferred symptoms are present in the symptom option list, the inferred symptoms are listed in a descending order according to the certainty values of the inferred symptoms. The medical knowledge base comprises information from healthcare authorities, wherein the information is clinical data. The user terminal is a personal computer or a mobile device. The inferred symptom in the symptom option list is presented in the form of text, image, a region of body on a 3-dimensional body map, or a combination thereof.

Another aspect of the present invention is to provide a system for providing a knowledge-based personal intelligent health consultation, the system comprising: a user interface for providing a symptom option list or a health consultation to a user terminal and receiving a symptom selection set from the user terminal; a medical knowledge base including a vast amount of information regarding diseases and symptoms, the correlations between diseases and symptoms are specifically evaluated using a weighted AND-OR diagram; and an inference engine to infer at least one candidate disease from the medical knowledge base based on the symptom selection set received from the user terminal and assess a certainty value of the candidate disease; wherein when the certainty value of the candidate disease exceeds a predetermined threshold value, the health consultation is provided to the user terminal via the user interface, and wherein when the certainty value of the candidate disease fails to reach the predetermined threshold value, a symptom option list is generated by the inference engine and provided to the user terminal via the user interface.

For the system of the present invention, the inference engine interactively and adaptively adjusts the certainty values of symptoms and diseases based on the symptom selection set received from the user terminal. The symptom option list includes at least one inferred symptom, and when more than one inferred symptoms are present in the symptom option list, the inferred symptoms are listed in a descending order according to the certainty values of the inferred symptoms.

In one embodiment of the present invention, the inferred symptom in the symptom option list is presented in the form of text, image, a region of body on a 3-dimensional body map, or a combination thereof. The user terminal is a personal computer or a mobile device, and the medical knowledge base comprises information from healthcare authorities, wherein the information is clinical data.

The medical knowledge base of the present invention encompasses a vast amount of information regarding diseases and symptoms from a variety of sources, and the correlations between diseases and symptoms are specifically evaluated using a weighted AND-OR diagram. The inference engine of the present invention is capable of not only intelligently assess certainty values of individual diseases and symptoms presented in the medical knowledge base but also interactively and adaptively adjust the certainty values of symptoms and possible diseases based on the instant selection of a user. Hence, through the medical knowledge base and inference engine, the present invention provides a system which, by a series of guided interactions, asks right questions and allows the user to provide the right information so as to achieve accurate inference as soon as possible. Moreover, information and communication technology (ICT) along with mobile devices, such as smart phones and tablets, are also incorporated in the present invention to accomplish intelligent and personalized health consultations.

The present invention is further explained in the following embodiment illustration and examples. Those examples below should not, however, be considered to limit the scope of the invention, and it is contemplated that modifications will readily occur to those skilled in the art, which modifications will be within the spirit of the invention and scope of the appended claims.

DETAILED DESCRIPTION OF THE PREFERRED EMBODIMENT

Reference will now be made to the accompanying drawings, which at least will assist in illustrating the various pertinent features of the present invention. In this regard, the following description is presented for purposes of illustration and description and is not intended to limit the invention to the form disclosed herein. Consequently, variations and modifications commensurate with the following teachings, and skill and knowledge of the relevant art, are within the scope of the present invention. The embodiments described herein are further intended to enable others skilled in the art to utilize the invention as described or in other embodiments and with various modifications required by the particular applications or uses of the present invention.

Construction of Medical Knowledge Base

A medical knowledge base including networks of the correlations between diseases and the possible symptoms thereof is constructed. Multiple data resources are incorporated into the medical knowledge base of the present invention, for example, medical dictionaries and clinical data from National Health Insurance Database are utilized to construct a "static" knowledge base representing the relationships between diseases and symptoms. The medical knowledge base of the present invention covers large amount of information on diseases and their related symptoms, which promote the inference of possible diseases which a user is suffered from.

To establish the correlation between diseases and symptoms, the present invention utilizes AND-OR graphs to describe their relationships. Specifically, the logic units (AND/OR) are used to represent the complicated relationships between diseases and symptoms, for example, one disease can cause one or a plurality of symptoms; one symptom can be found in several diseases.

Figure 1:
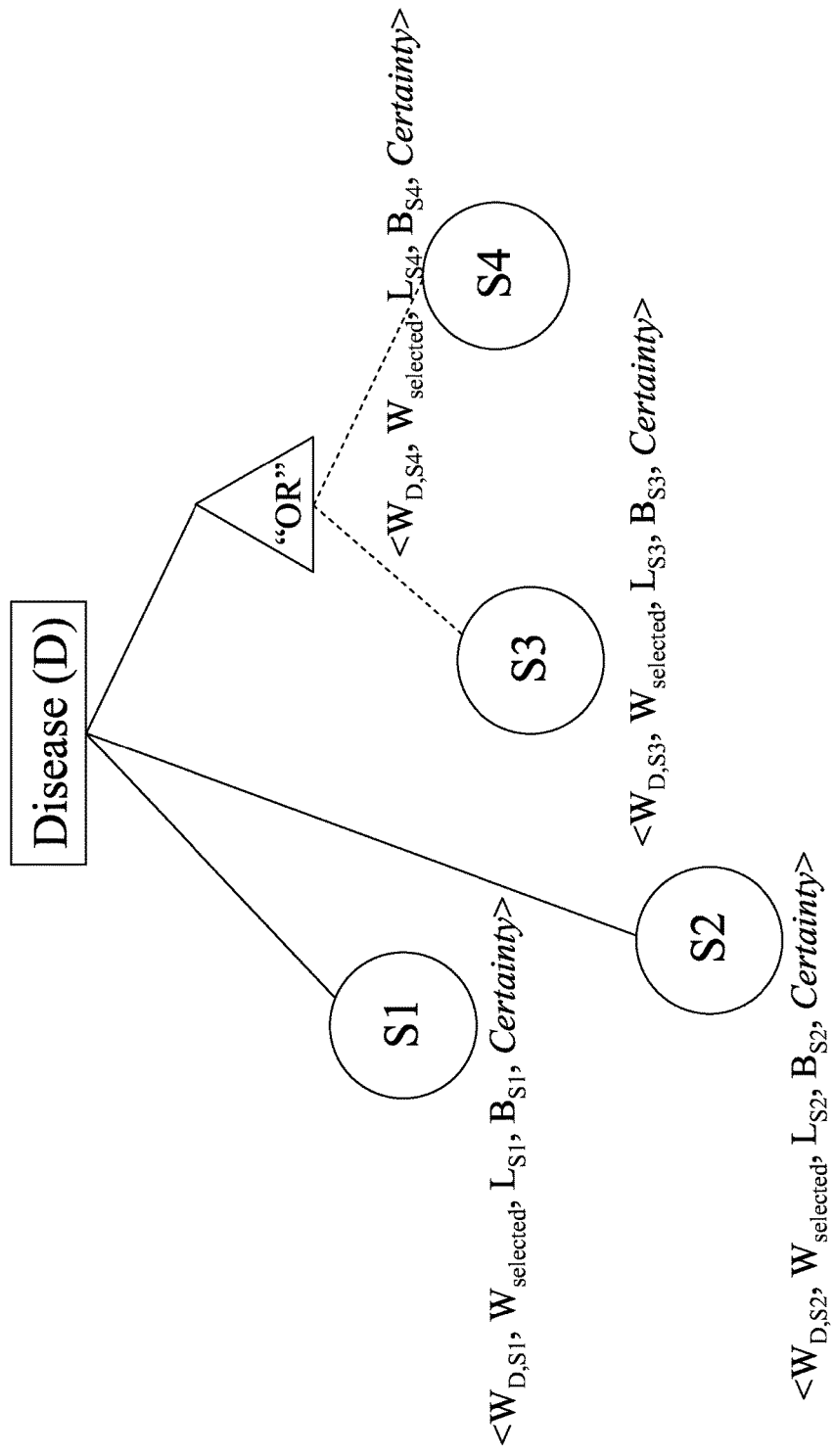
FIG. 1 shows an AND-OR graph of a disease, wherein four symptoms, namely S1, S2, S3, and S4, are found to be associated with the disease (D). The logic unit (illustrated as a triangle) is "OR" (note that a dotted line is used to link the leaf nodes thereunder), indicating that symptoms S3 or S4 can be found in a patient with disease (D). Each symptom is assigned a feature vector, which includes but is not limited to the following: the body part of occurrence (B), lesion (L), the weight of occurrence of the symptom ($W_{D,S}$), and the certainty value of the symptom (certainty).
Figure 2:
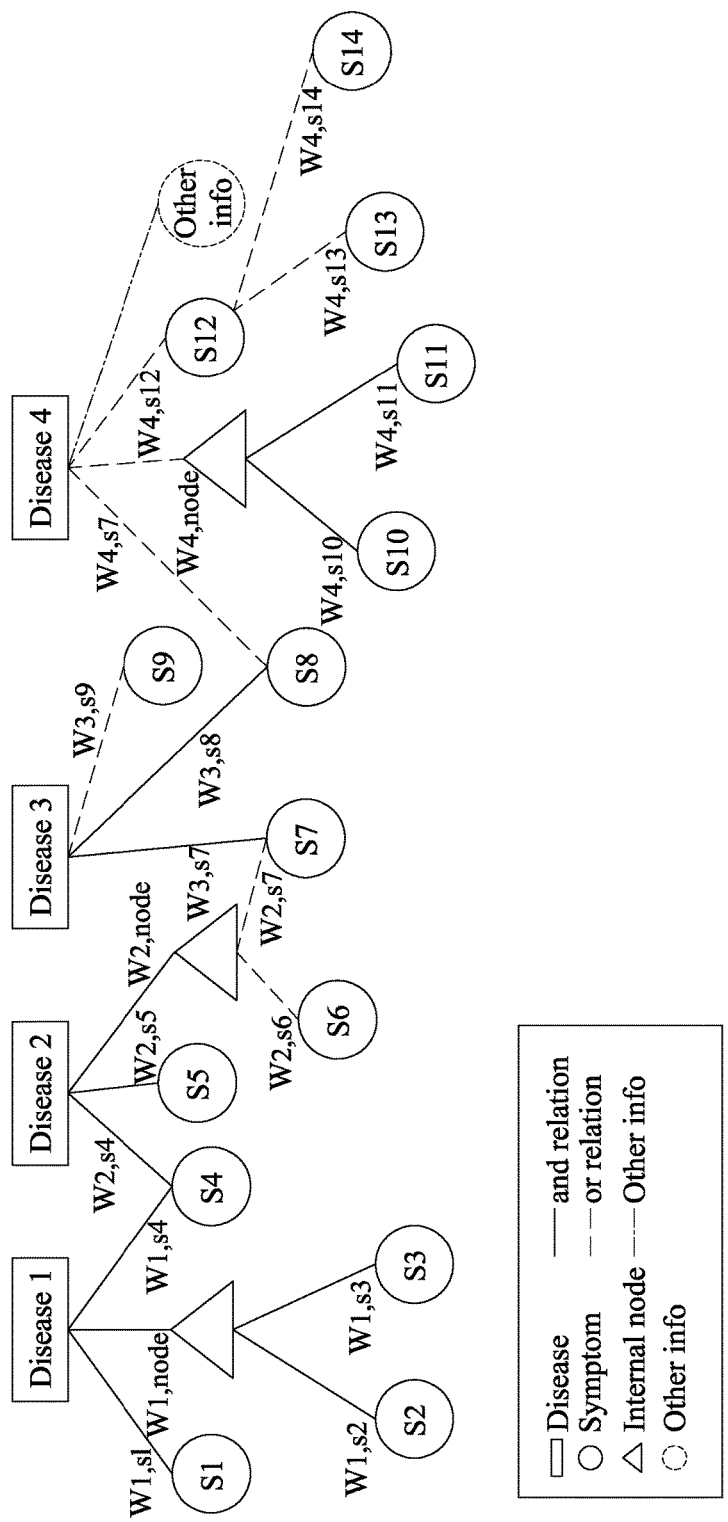
FIG. 2 shows the construction of medical knowledge base, wherein four interconnected AND-OR graphs of four individual diseases with a total number of 14 different symptoms are illustrated herein.

For each disease, an AND-OR graph is established. In the AND-OR graph, a root node represents a disease and a plurality of leaf nodes of said root node represent symptoms related to said disease. The internal nodes represent the logic units used to describe the occurrence conditions of symptoms. As shown in FIG. 1, the logic unit is "OR", indicating that symptoms S3 or S4 can be found in a patient with disease (D). As illustrated in FIG. 2, four interconnected AND-OR graphs of four individual diseases with a total number of 14 different symptoms form the framework of the medical knowledge base of the present invention.

For the "static" data structure of the medical knowledge base of the present invention, the initial value of the occurrence is determined based on, for example, the information, and particularly clinical data, obtained from National Health Insurance Database. For the "dynamic" data structure of the medical knowledge base of the present invention, the certainty values of all possible symptoms and diseases are re-calculated during each round of interaction by the inference engine according to the state of the current interaction. Then, an algorithm was designed to propose questions (symptoms) to the user so as to proceed to the next round of interaction. Thus, the dynamic data structure of the medical knowledge base of the present invention is a "dynamic weighted AND-OR diagram", AND-OR represents the correlation between diseases and symptoms. Sometimes the occurrences of certain symptoms are all required, while sometimes the occurrence of only one or several symptoms suffices. In addition, it is possible for the above circumstances to occur simultaneously.

Calculation of the Weight of Occurrence of a Symptom

For each symptom of an AND-OR graph (FIG. 1), a feature vector is used to describe its characteristics. Such feature vector includes but is not limited to the following: the body part of occurrence (defined as B, ie. face), lesion (defined as L, ie. rash), the weight of occurrence (defined as $W_{D,S}$), and the certainty values of symptoms (defined as certainty).

Figure 3:
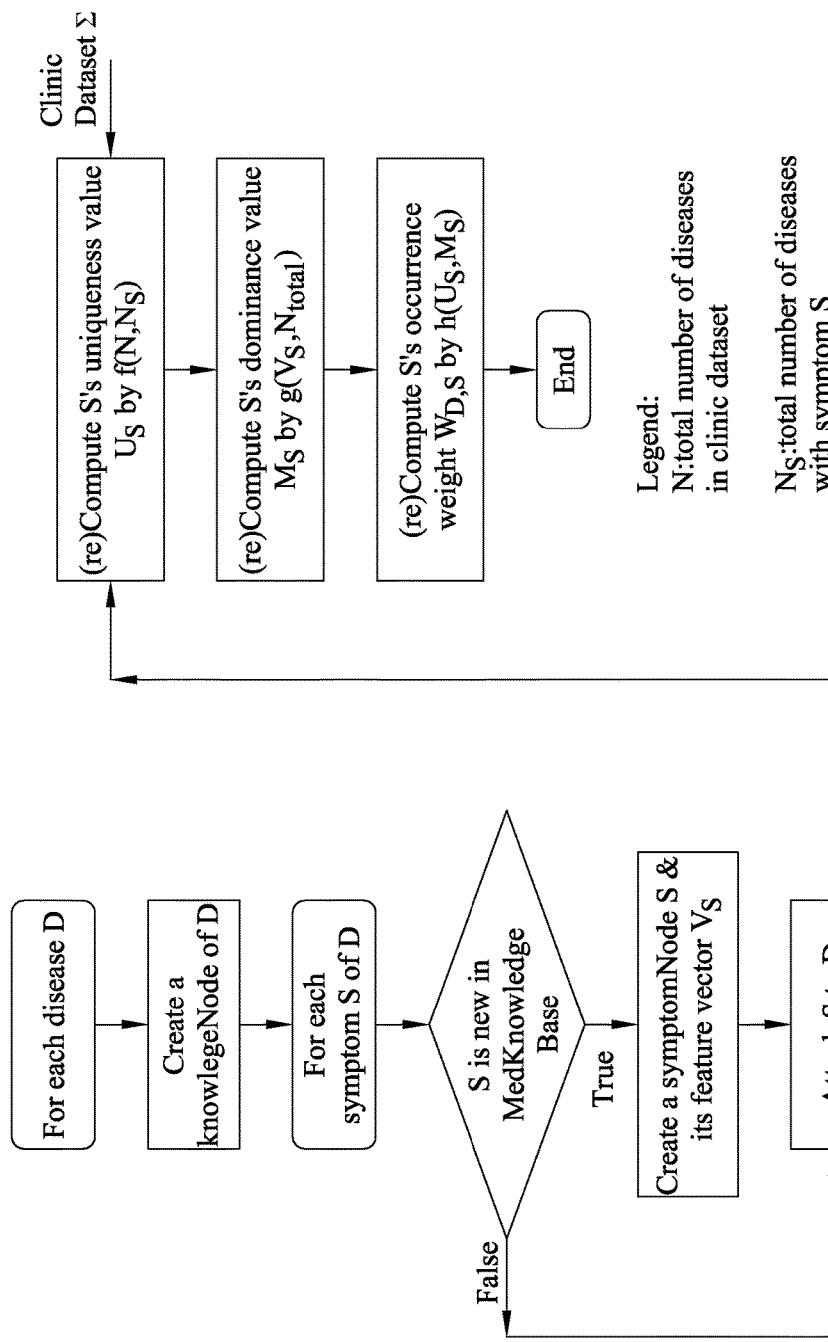
FIG. 3 illustrates the algorithm for determining the weight of occurrence of a symptom (S) to a disease (D), $W_{D,S}$, which is calculated by the integration of the uniqueness ($U_S$) of said symptom among all diseases and the dominance ($M_S$) of said symptom in a specific disease.

When constructing the medical knowledge base of the present invention, a weight of occurrence, $W_{D,S}$, is assigned to each symptom. The greater the $W_{D,S}$, the more essential a symptom is to its corresponding disease. The algorithm for calculating the weight of occurrence of a symptom is shown in FIG. 3. Considering the fact that one symptom can be found in several diseases and one disease usually involves a plurality of symptoms, the "uniqueness" (indicated as $U_S$) of said symptom among all diseases and the "dominance" (indicated as $M_S$) of said symptom to a specific disease are computed in accordance with the clinical data gathered from National Health Insurance Database. The uniqueness of a symptom is a function of the total number of diseases in clinic dataset and the total number of diseases with said symptom. The dominance of a symptom represents the weight of said symptom in a specific disease as opposed to all other possible symptoms. Eventually, the weight of occurrence of a symptom (S) to a disease (D), $W_{D,S}$, is calculated by the integration of $U_S$ and $M_S$.

During each round of interaction, the weight of occurrence of a symptom is re-calculated according to the user input. The certainty value of said symptom and that of a related disease are also re-calculated, which leads to a revised health consultation.

In addition, the medical knowledge base also incorporates supplementary information from diagnosis accumulated in the National Health Insurance Database such as gender, season, region, etc., into the disease for the purpose of achieving more accurate inference.

Interactive and Adaptive Inference Engine

The inference process of the present invention is interactive and adaptive since an inference engine of the present invention is configured to interact with the user by responding with the most relevant question(s) based on the information provided by the user. The system of the present invention not only provides symptoms and the occurrence thereof based on the "static data" of the medical knowledge Inference base, but also "dynamically" and continuously adjusts the certainty values of said symptoms and possible diseases so as to infer the most possible diseases or symptoms for the user.

Figure 4:
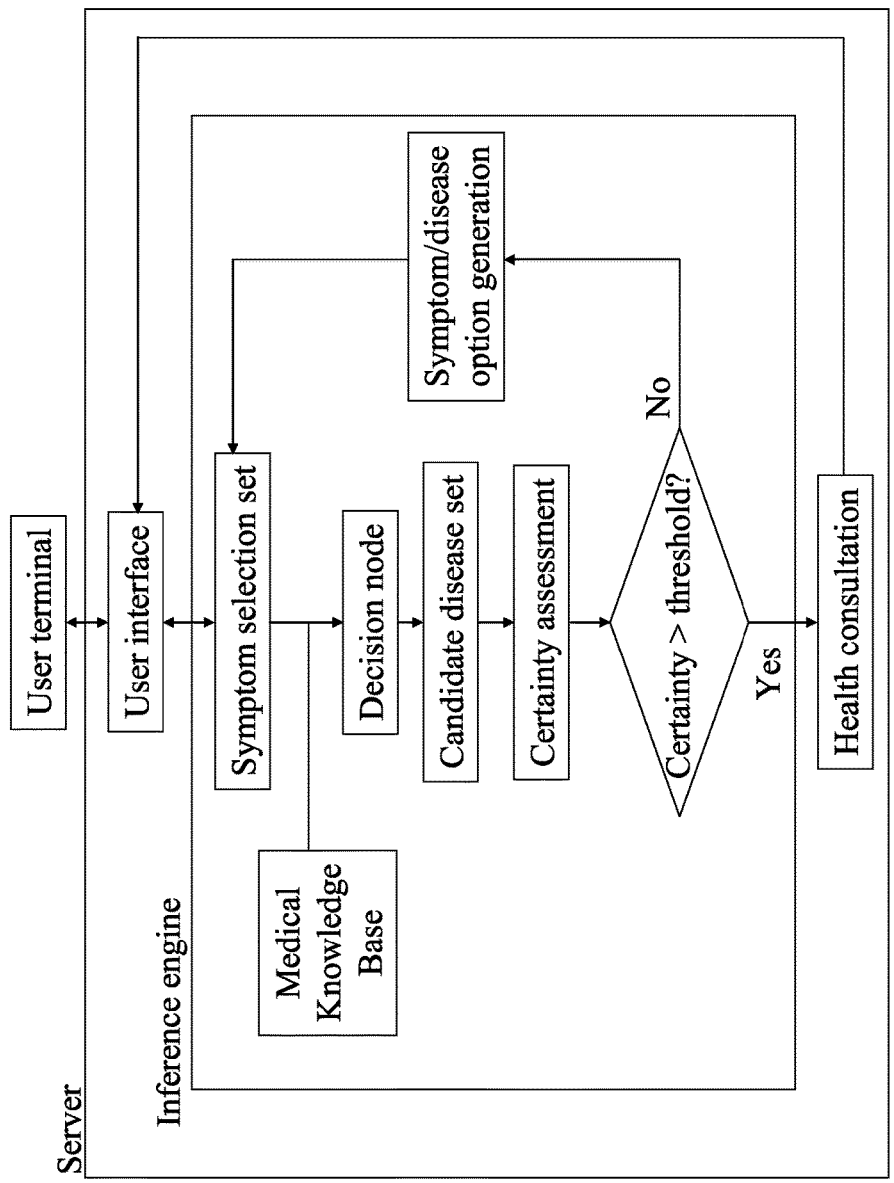
FIG. 4 illustrates the system for providing a knowledge-based personal intelligent health consultation of the present invention.

In order to obtain a knowledge-based personal intelligent health consultation, the system of the present invention use a plurality of decision nodes which utilize the information in the medical knowledge base constructed above. FIG. 4 illustrates the process of the interactive and adaptive knowledge-based personal intelligent health inference of the present invention. Firstly, at the beginning of each round, the user selects from, for example, text, image, or a region of a body on a 3-dimensional body map displayed on the user terminal Such selections are stored in a symptom selection set. The inference engine then infers candidate diseases from the medical knowledge base based on the information received in the symptom selection set. After obtaining or revising the candidate disease set, a certainty assessment is performed to assess the likelihood (certainty) of the possible diseases in the candidate disease set which is related to the information (symptoms) entered by the user. On one hand, if the certainty value of a candidate disease exceeded a threshold value predetermined by the system, say, 80%, the disease is deemed highly possible and is presented to the user along with the health consultation thereof via the user interface. The inference is, thus, completed. On the other hand, if the certainty value of a candidate disease failed to reach the predetermined threshold value, a symptom/disease option generation is performed to re-calculate the certainty value of the each individual candidate disease and the symptoms thereof based on the information entered by the user and the correlation network of disease and symptom in the medical knowledge base so as to infer and propose the most relevant disease or symptoms. Such inferred and proposed new diseases or symptoms are then presented to the user via a ranking and presentation layout on the user terminal as text, image, or a region of a body on a 3-dimensional body map for the user to select so as to proceed to the next round.

As set forth above, three major algorithms, namely "certainty assessment", "symptom/disease option generation", and "ranking and presentation layout" are encompassed in the process of inference and are elaborated as follows.

Certainty Assessment

Figure 5:
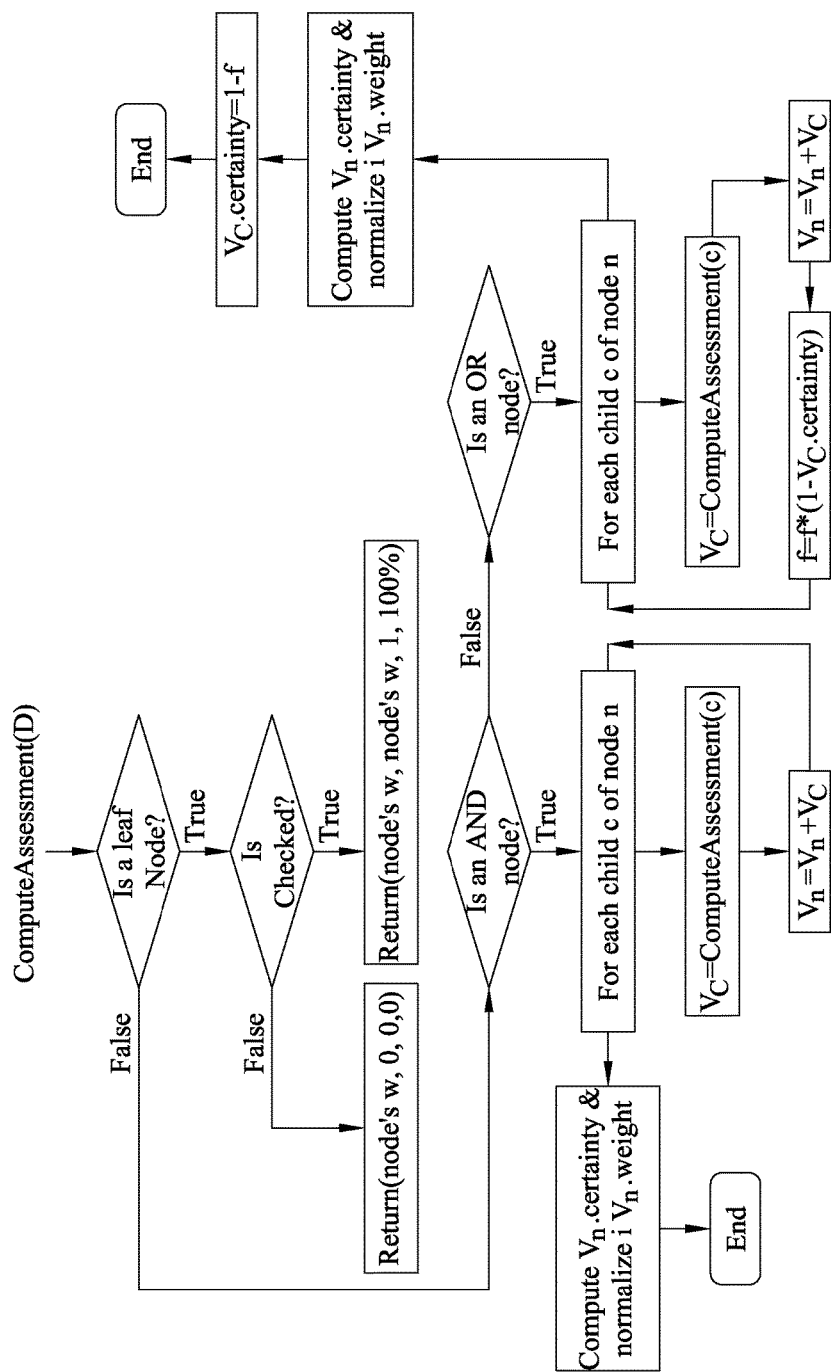
FIG. 5 illustrates the algorithm for certainty assessment. The certainty value of a candidate disease is calculated by using the certainty values of the related symptoms and the logic units according to a user input.

Certainty assessment is the algorithm for calculating the certainty values of symptoms and the logic units to a candidate disease set. Also, the certainty assessment calculates the certainty value of each individual candidate disease among the current candidate disease set. Recursive function as well as depth-first search method are used to browse the AND-OR graph of a candidate disease in a downward manner starting from the root. For each node in the AND-OR graph, a feature vector is assigned to record the information of said node. The format of the feature vector is as follows: <weight, $weight_{selected}$, $weight_{normalized}$, certainty>. "Weight" represents the sum of the weights of occurrence of said node (including its children nodes); $weight_{selected}$ records the sum of the weights of occurrence of said node (including its children nodes) selected by the user; $weight_{normalized}$ is $weight_{selected}$/weight. "Certainty" represents the level of certainty of said node and is in the range of 0 to 100%. As shown in FIG. 5, the certainty value of a candidate disease is calculated by using the certainty values of symptoms and the logic units according to the user input.

Symptom/Disease Option Generation

In order to propose the most relevant question, the system of the present invention executes a symptom/disease option generation algorithm, which browses the AND-OR graph of each candidate disease using a depth-first search and infers the exact symptom options for the user in regard to the different logic units and certainty values of the nodes. The symptom options inferred are listed in a symptom option list, in which the options are arranged in a descending order according to the certainty values of the symptoms and related logic units. Such list can be further presented and emphasized on a user terminal to assist and guide the users to accurately identify their disease or symptoms.

Briefly, the operative rules of the symptom/disease option generation algorithm are described as follows:

- if the certainty value of a node (n) visited is 100%, the visit to its child nodes stops. (Note: n can be a root node, an internal node, or a leaf node);
- if the node (n) visited is a leaf node, the corresponding symptom is added to the symptom option list;
- if the node (n) visited is an internal node and the logic unit thereof is "AND", each child node thereunder is visited. The child nodes are sorted according to their (weight-$weight_{selected}$) and are visited individually;
- if the node (n) visited is an internal node and the logic unit thereof is "OR", each child node thereunder is visited. The child nodes are sorted according to their certainty values and are visited individually.

Through this algorithm set forth above, all possible symptom options can be generated for each candidate disease.

Ranking and Presentation Layout

During each round of interaction, the system of the present invention records candidate disease set related to the object instance and, through certainty assessment and symptom/disease option generation, the certainty value of each candidate disease in the candidate disease set can be calculated so as to generate symptom options for said candidate disease. By presenting the information acquired using the ranking and presentation layout algorithm, the system of the present invention is able to guide the user to enter information that most likely represents the health condition of the user via an interactive dialogue. In other words, the user is guided to provide "appropriate" information to the system providing more accurate inference. Through such interactive dialogue of each round of guided consultation, the system of the present invention asks the right questions and allows the user to enter the right information to obtain the final consultation as soon as possible. Those questions are given based on the information already entered by the user and the current inference and are arranged in a descending order according to their weighted certainty values so as to distinguish different diseases. In addition, diseases and symptoms thereof are presented based on the AND-OR relationship therebetween.

In summary, for each round of the inference process of the present invention, the most relevant symptoms or diseases are inferred and proposed according to the certainty values of the symptoms and possible disease selected by the user. Specifically, more accurate consultation of possible symptoms are provided in order to exceed the predetermined threshold value as soon as possible.

In addition, regarding the logical AND/OR operation, forward-chaining and backward-chaining methods are utilized, yet, one AND-OR diagram of the medical knowledge base of the present invention encompasses an attribute vector that describes said logic node. The attribute vector includes the certainty of an object instance thereupon during the interactive consulting process. (Note that each round of operation of a user using the knowledge-based personal intelligent health consulting system is defined as an "object instance", since the inferred result of each interactive consultation would vary according to the different information entered/selected by the user). Due to the fact that the weighted certainty values are considered, through backward-chaining, the inference engine is able to intelligently fish out the imperative symptoms to be proposed. Furthermore, the questions proposed are in order of precedence. As a result, the algorithms utilized herein are defined as "weighted forward-chaining and weighted backward-chaining algorithms".

The method and system of the present invention is applicable and valuable to the industry. Those embodiments above are better operations, and should not, however, be considered to limit the scope of the invention, it is contemplated that modifications will readily occur to those skilled in the art, which modifications will be within the spirit of the invention and scope of the appended claims.

What is claimed is:

1. A method for providing a knowledge-based personal intelligent health consultation, the method comprising:
   providing a symptom option list to a user terminal and receiving a symptom selection set from the user terminal;
   inferring at least one candidate disease from a medical knowledge base based on the symptom selection set received from the user terminal, wherein the medical knowledge base includes a vast amount of information regarding diseases and symptoms, the correlations between diseases and symptoms are specifically evaluated using a weighted AND-OR diagram;
   assessing a certainty value of the candidate disease; and
   providing a health consultation to the user terminal when the certainty value of the candidate disease exceeds a predetermined threshold value, or providing a symptom option list generated by an inference engine to the user terminal when the certainty value of the candidate disease fails to reach the predetermined threshold value;
   wherein the symptom is represented by a feature vector in the medical knowledge base, the feature vector includes at least body part, lesion, a weight of occurrence, and the certainty value of the candidate disease.

2. The method of claim 1, wherein the inference engine interactively and adaptively adjusts a certainty value of the symptoms and the certainty value of the candidate disease based on the symptom selection set received from the user terminal.

3. The method of claim 1, wherein the weight of occurrence is calculated according to the uniqueness and dominance of the symptom to the disease.

4. The method of claim 1, wherein the medical knowledge base comprises information from healthcare authorities.

5. The method of claim 4, wherein the information is clinical data.

6. The method of claim 1, wherein the symptom option list generated by the inference engine comprises at least one inferred symptom, and when more than one inferred symptoms are present in the symptom option list, the inferred symptoms are listed in a descending order according to the certainty values of the inferred symptoms.

7. The method of claim 6, wherein the inferred symptom in the symptom option list is presented in the form of text, image, a region of a body on a 3-dimensional body map, or a combination thereof.

8. The method of claim 1, wherein the user terminal is a personal computer or a mobile device.

9. A system for providing a knowledge-based personal intelligent health consultation, the system comprising:
   a user interface for providing a symptom option list or a health consultation to a user terminal and receiving a symptom selection set from the user terminal;
   a medical knowledge base including a vast amount of information regarding diseases and symptoms, the correlations between diseases and symptoms are specifically evaluated using a weighted AND-OR diagram; and
   an inference engine to infer at least one candidate disease from the medical knowledge base based on the symptom selection set received from the user terminal and assess a certainty value of the candidate disease;
   wherein when the certainty value of the candidate disease exceeds a predetermined threshold value, the health consultation is provided to the user terminal via the user interface, and when the certainty value of the candidate disease fails to reach the predetermined threshold value, the symptom option list is generated by the inference engine and provided to the user terminal via the user interface; and
   wherein the symptom is represented by a feature vector in the medical knowledge base, the feature vector includes at least body part, lesion, a weight of occurrence, and the certainty value of the candidate disease.

10. The system of claim 9, wherein the inference engine interactively and adaptively adjusts a certainty value of the symptoms and the certainty value of the candidate disease based on the symptom selection set received from the user terminal.

11. The system of claim 9, wherein the symptom option list includes at least one inferred symptom, and when more than one inferred symptoms are present in the symptom option list, the inferred symptoms are listed in a descending order according to the certainty values of the inferred symptoms.

12. The system of claim 11, wherein the inferred symptom in the symptom option list is presented in the form of text, image, a region of a body on a 3-dimensional body map, or a combination thereof.

13. The system of claim 9, wherein the user terminal is a personal computer or a mobile device.

14. The system of claim 9, wherein the medical knowledge base comprises information from healthcare authorities.

15. The system of claim 14, wherein the information is clinical data.

* * * * *